United States Patent
Chang et al.

(10) Patent No.: US 8,748,354 B2
(45) Date of Patent: Jun. 10, 2014

(54) RNA INTERACTOME ANALYSIS

(75) Inventors: Howard Yuan-Hao Chang, Stanford, CA (US); Ci Chu, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/569,005

(22) Filed: Aug. 7, 2012

(65) Prior Publication Data

US 2013/0123123 A1  May 16, 2013

Related U.S. Application Data

(60) Provisional application No. 61/521,716, filed on Aug. 9, 2011.

(51) Int. Cl.
*C40B 30/04* (2006.01)
*C12Q 1/68* (2006.01)

(52) U.S. Cl.
USPC ............................................. 506/9; 435/6.11

(58) Field of Classification Search
None
See application file for complete search history.

(56) References Cited

U.S. PATENT DOCUMENTS

2012/0115237 A1* 5/2012 Smart et al. .................... 436/86

FOREIGN PATENT DOCUMENTS

WO   WO 2009024781 A1 * 2/2009 ............... C12Q 1/68

OTHER PUBLICATIONS

Ule et al. (2003)"CLIP Identifies Nova-Regulated RNA Networks in the Brain" Science 302(5648):1212-1215.*
Simon et al. (2011) "The genomic binding sites of a noncoding RNA" PNAS 108(51):20497-20502.*
Kiernan (2000) "Formaldehyde, formalin, paraformaldehyde and glutaraldehyde: What they are and what they do" Microscopy Today 00-1:8-12.*
Gresham et al. (2010) "Optimized detection of sequence variation in heterozygous genomes using DNA microarrays with isothermal-melting probes" PNAS 107(4):1482-1487.*
Guerrero; et al., "An integrated mass spectrometry-based proteomic approach: quantitative analysis of tandem affinity-purified in vivo cross-linked protein complexes (QTAX) to decipher the 26 S proteasome-interacting network", Molecular & Cell Proteomics (Feb. 2006), 5(2):366-78.
Kuhn-Holsken; et al., "Complete MALDI-ToF MS analysis of cross-linked peptide-RNA oligonucleotides derived from nonlabeled UV-irradiated ribonucleoprotein particles", RNA Society (Dec. 2005), 11(12):1915-30.
Rhode; et al., "Analysis of site-specific protein-RNA cross-links in isolated RNP complexes, combining affinity selection and mass spectrometry", RNA Society (Dec. 2003), 9(12):1542-51.
Slobodin; et al., "A novel mRNA affinity purification technique for the identification of interacting proteins and transcripts in ribonucleoprotein complexes", RNA Society (Nov. 2010), 16(11)2277-90.
Urlaub; et al., "A general approach for identification of RNA-protein cross-linking sites within native human spliceosomal small nuclear ribonucleoproteins (snRNPs). Analysis of RNA-protein contacts in native U1 and U4/U6.U5 snRNPs", The Journal of Biological Chemistry (Dec. 2000), 275(52):41458-68.

* cited by examiner

*Primary Examiner* — Tracy Vivlemore
*Assistant Examiner* — Karen S Weiler
(74) *Attorney, Agent, or Firm* — Bozicevic, Field & Francis LLP; James S. Keddie

(57) ABSTRACT

A method of sample analysis is provided. In certain cases, the method comprises: a) cross-linking the contents of a cell using a heat stable crosslinking agent to produce cross-linked ribonucleotide complexes; b) fragmenting the cross-linked ribonucleotide complexes to produce complexes comprising protein, RNA fragments and, optionally, genomic DNA fragments; c) contacting the complexes with a plurality of non-overlapping oligonucleotides comprise an affinity tag and that are complementary to a specific target RNA of the cell under high stringency conditions that include high temperature; d) isolating complexes that contain the oligonucleotides using the affinity tag to produce isolated complexes; e) enzymatically releasing the protein, RNA fragments and/or the genomic DNA fragments from the isolated complexes to produce a released component, without reversing the crosslinking; and f) analyzing the released component.

14 Claims, 10 Drawing Sheets

```
SEQUENCE LISTING

<160> NUMBER OF SEQ ID NOS: 6

<210> SEQ ID NO 1
<211> LENGTH: 25
<212> TYPE: DNA
<213> ORGANISM: Artificial sequence
<220> FEATURE:
<223> OTHER INFORMATION: Synthetic Morpholino probe for hybridization
      with an RNA target
<220> FEATURE:
<221> NAME/KEY: misc_feature
<222> LOCATION: (1)..(25)
<223> OTHER INFORMATION: This sequence is a morpholino probe that is
      designed to hybridize with an RNA target sequence.

<400> SEQUENCE: 1
gagcagctca agtcccctgc atcca                                           25

<210> SEQ ID NO 2
<211> LENGTH: 25
<212> TYPE: DNA
<213> ORGANISM: Artificial sequence
<220> FEATURE:
<223> OTHER INFORMATION: Synthetic Morpholino probe to hybridize with
      RNA target
<220> FEATURE:
<221> NAME/KEY: misc_feature
<222> LOCATION: (1)..(25)
<223> OTHER INFORMATION: This sequence is a morpholino probe that is
      designed to hybridize with an RNA target sequence.

<400> SEQUENCE: 2 gcaccccgctc aggttttttcc agcgt                                          25

<210> SEQ ID NO 3
<211> LENGTH: 26
<212> TYPE: DNA
<213> ORGANISM: Artificial sequence
```

-continued

```
<220> FEATURE:
<223> OTHER INFORMATION: Synthetic Morpholino probe to hybridize with
      RNA target
<220> FEATURE:
<221> NAME/KEY: misc_feature
<222> LOCATION: (1)..(26)
<223> OTHER INFORMATION: This sequence is a morpholino probe that is
      designed to hybridize with an RNA target sequence.

<400> SEQUENCE: 3
tacataaacc tctgttctgt gagtgc                                            26

<210> SEQ ID NO 4
<211> LENGTH: 25
<212> TYPE: DNA
<213> ORGANISM: Artificial sequence
<220> FEATURE:
<223> OTHER INFORMATION: Synthetic Morpholino probe to hybridize with
      RNA target
<220> FEATURE:
<221> NAME/KEY: misc_feature
<222> LOCATION: (1)..(25)
<223> OTHER INFORMATION: This sequence is a morpholino probe that is
      designed to hybridize with an RNA target sequence.

<400> SEQUENCE: 4
cctcttacct cagttacaat ttata                                             25

<210> SEQ ID NO 5
<211> LENGTH: 30
<212> TYPE: DNA
<213> ORGANISM: Artificial sequence
<220> FEATURE:
<223> OTHER INFORMATION: Synthetic Nucleic Acid

<400> SEQUENCE: 5
ccctaaccct aaccctaacc ctaaccctaa                                        30

<210> SEQ ID NO 6
<211> LENGTH: 30
<212> TYPE: DNA
<213> ORGANISM: Artificial sequence
<220> FEATURE:
<223> OTHER INFORMATION: Synthetic Nucleic Acid

<400> SEQUENCE: 6
gtgatccgcc cgcctcggcc tcccaaagtg                                        30
```

RNA INTERACTOME ANALYSIS

CROSS-REFERENCING

This patent application claims the benefit of U.S. provisional application Ser. No. 61/521,716, filed on Aug. 9, 2011, which application is incorporated by reference herein.

GOVERNMENT RIGHTS

This invention was made with Government support under contract R01-CA118750 awarded by the National Institutes of Health. The Government has certain rights in this invention.

INTRODUCTION

It is of great interest to researchers to isolate and characterize the cellular components, e.g., protein, RNA and genomic DNA, that are bound to a particular RNA within a cell. For example, long noncoding RNAs (lncRNAs) are key regulators of chromatin states for important biological processes such as dosage compensation, imprinting, and developmental gene expression. The recent discovery of thousands of lincRNAs in association with specific chromatin modification complexes, such as Polycomb Repressive Complex 2 (PRC2) that mediates histone H3 lysine 27 trimethylation (H3K27me3), suggests broad roles for numerous lincRNAs in managing chromatin states in a gene-specific fashion. While some lincRNAs are thought to work in cis on neighboring genes, other lincRNAs work in trans to regulate distantly located genes. For instance, *Drosophila* ncRNAs roX1 and roX2 bind numerous regions on the X chromosome of male cells, and are critical for dosage compensation. However, the exact locations of their binding sites are not known at high resolution. Similarly, human lincRNA HOTAIR can affect PRC2 occupancy on hundreds of genes genome-wide, but how specificity is achieved is unclear. LincRNAs can also serve as modular scaffolds to recruit the assembly of multiple protein complexes. The classic trans-acting RNA scaffold is the TERC RNA that serves as the template and scaffold for the telomerase complex; HOTAIR can also serve as a scaffold for PRC2 and a H3K4 demethylase complex. Prior studies mapping RNA occupancy at chromatin have revealed some insights but only at single gene locus at a time. The occupancy sites of most lincRNAs are not known, and the roles of lincRNAs in chromatin regulation have been mostly inferred from the indirect effects of lincRNA perturbation.

SUMMARY

A method of sample analysis is provided. In certain cases, the method comprises: a) cross-linking the contents of a cell using a heat stable crosslinking agent to produce cross-linked ribonucleotide complexes; b) fragmenting the cross-linked ribonucleotide complexes to produce complexes comprising protein, RNA fragments and, optionally, genomic DNA fragments; c) contacting the complexes with a plurality of non-overlapping oligonucleotides comprise an affinity tag and that are complementary to a specific target RNA of the cell under high stringency conditions that include high temperature; d) isolating complexes that contain the oligonucleotides using the affinity tag to produce isolated complexes; e) enzymatically releasing the protein, RNA fragments and/or genomic DNA fragments from the isolated complexes to produce a released component, without reversing the crosslinking; and f) analyzing the released component. The method may be used to analyze RNA, protein and/or genomic DNA that is present in a complex.

DEFINITIONS

Figure 1:
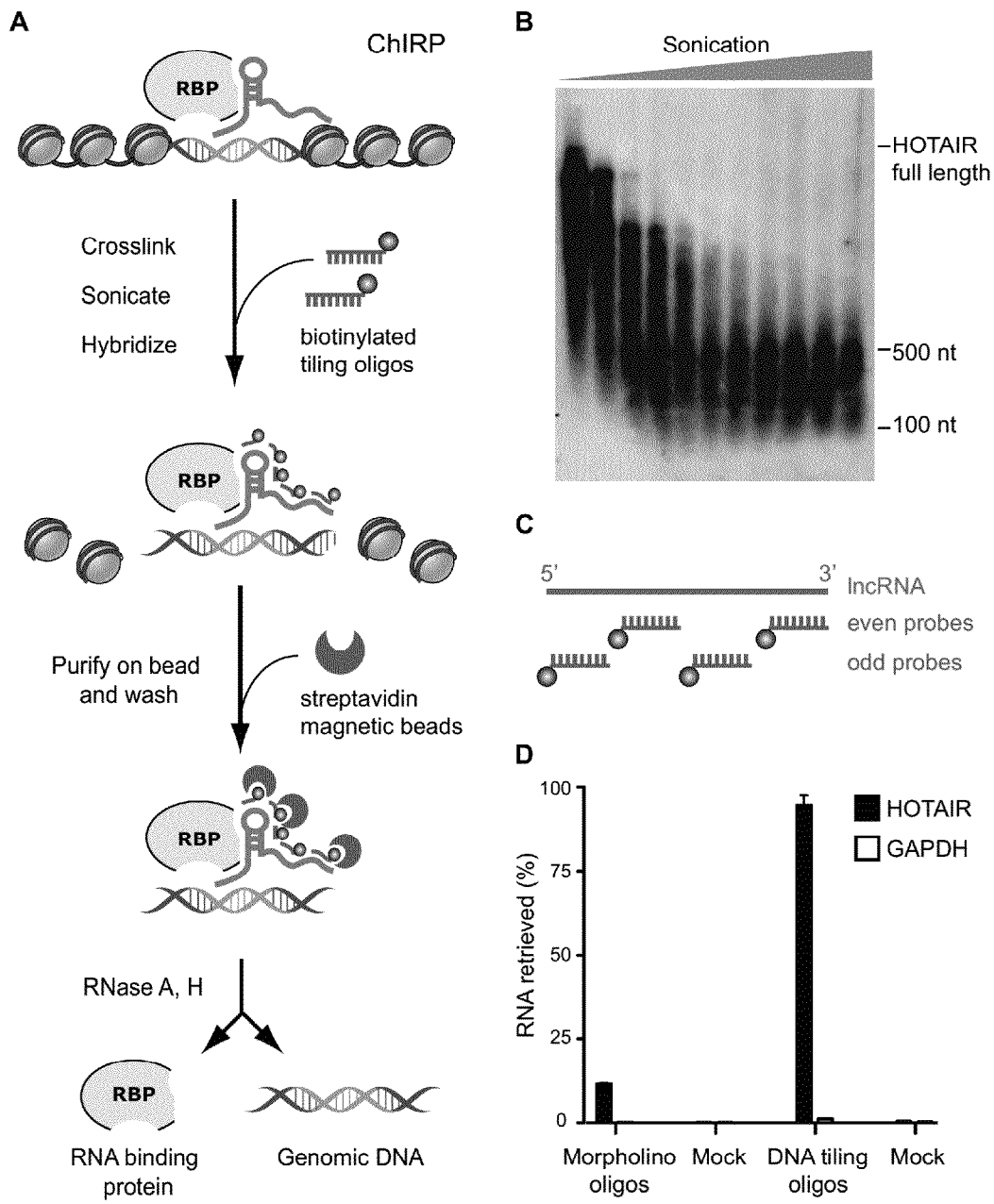
FIG. 1 Chromatin isolation by RNA purification. (A) Workflow of ChIRP. Chromatin is crosslinked to lincRNA: protein adducts in vivo. Biotinylated tiling probes are hybridized to target lncRNA, and chromatin complexes are purified using magnetic streptavidin beads, followed by stringent washes. We elute lncRNA bound DNA or proteins with a cocktail of Rnase A and H. A putative lincRNA binding sequence is schematized in orange. (B) Northern blot shows HOTAIR RNA is sheared into the size range of 100-500 nt by sonication. (C) Design of antisense DNA tiling probes, grouped into "even" and "odd" sets based on their positions along the RNA. (D) Complementary DNA tiling oligonucleotides effectively retrieve ~95% of HOTAIR RNA from chromatin, as compared to ~10% by morpholino probes.

Unless defined otherwise, all technical and scientific terms used herein have the same meaning as commonly understood by one of ordinary skill in the art to which this invention belongs. Still, certain terms are defined below for the sake of clarity and ease of reference.

As used herein, the terms "polypeptide" and "protein" are used interchangeably. The term "polypeptide" also includes post-translationally modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 9, 10, 20, 30 or 50 amino acids. In some embodiments, peptides are between 5 and 30 amino acids in length. A peptide may be made by protease digestion of a large polypeptide.

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarity may be calculated to assess the possibility of a non-specific (off-target) binding. In general, a complementarity of 50% or less does not lead to non-specific binding. In addition, a complementarity of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from 2 to 200 nucleotides (e.g., 25 to 200 nucleotides) and up to 500 nucleotides in length. Oligonucleotides may be synthetic and, in certain embodiments, are less than 300 nucleotides in length. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example. Oligonucleotides may be DNA, RNA, DNA/RNA and in certain cases may contain modified/synthetic backbone (e.g. may be a 2-O-methyl oligonucleotide, PNA, or LNA) or base analogs of the four naturally occurring bases.

The term "sample" as used herein relates to a material or mixture of materials, typically, although not necessarily, in fluid form, containing one or more components of interest.

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions. In the subject assay, stringent hybridization conditions are at least as stringent as incubation in hybridization buffer (500 mM NaCl, 1% SDS, 100 mM Tris 7.0, 10 mM EDTA, 15% Formamide) at 37° C. for four hours.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determines whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C., a salt concentration of about 0.15 M NaCl at 72° C. for about 15 minutes, or a salt concentration of about 0.2×SSC at a temperature of at least about 50° C. or about 55° C. to about 60° C. for about 15 to about 20 minutes. Alternatively, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

The terms "hybridizing" and "binding", with respect to nucleic acids, are used interchangeably.

The terms "plurality", "set", "population", and "pool" are used interchangeably to mean at least 2, at least 10, at least 100, at least 500, at least 1000, at least 10,000, at least 100,000, at least 1000,000, at least 10,000,000, at least 100,000,000, or more.

The phrase "tiled probes" refers to non-overlapping probes that are designed to span or "tile" across an RNA of interest. Tiled probes are spaced farther apart by at least 1 nt, e.g., 15-80 nt.

As used herein, the term "affinity tag" refers to a member of a specific binding pair, i.e. two molecules where one of the molecules through chemical or physical means specifically binds to the other molecule. The complementary member of the specific binding pair may be immobilized (e.g., to a chromatography support, a bead or a planar surface) to produce an affinity chromatography support that specifically binds the affinity agent. Tagging a compound of interest with an affinity agent allows the compound to be separated from a mixture of untagged compounds using affinity chromatography. The specific binding pair are sometimes referred to as a ligand and receptor, although two complementary polynucleotide sequences (including nucleic acid sequences used as probes and capture agents in DNA hybridization assays) are also specific binding pairs, as are antibody and antigen, peptide-MHC antigen and T cell receptor, biotin and streptavidin pairs, etc. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc., so long as an epitope is present.

As used herein, the terms "biotin moiety" and "biotinylated" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$ M. A biotin affinity agent may also include a linker, e.g., -LC-biotin, -LC-LC-Biotin, -SLC-Biotin or -PEG$_n$-Biotin where n is 3-12.

As used herein, the term "crosslinking" refers to a reaction in which a covalent bond is formed. As used herein, the term "cross-linking" in the context of crosslinking cells refers to the cross-linking of the intracellular contents of cells, rather than the cross-linking of cells to one another.

As used herein, the term "covalently crosslinked" refers to two moieties that are linked to each other via covalent bonds.

As used herein, the term "heat stable crosslinking agent" is one that produces cross-links that remain at least 90% intact in aqueous solution at 37° C. for at least 6 hours.

Before the present invention is described in greater detail, it is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The headings provided herein are not limitations of the various aspects or embodiments of the invention. Accordingly, the terms defined immediately below are more fully defined by reference to the specification as a whole.

DETAILED DESCRIPTION OF EXEMPLARY EMBODIMENTS

As noted above, a method of sample analysis is provided. In certain cases, the method comprises: a) cross-linking the contents of a cell using a heat stable crosslinking agent to produce cross-linked ribonucleotide complexes; b) fragmenting the cross-linked ribonucleotide complexes to produce complexes comprising protein, RNA fragments and, optionally, genomic DNA fragments; c) contacting the complexes with a plurality of non-overlapping oligonucleotides comprise an affinity tag and that are complementary to a specific target RNA of the cell under high stringency conditions that include high temperature; d) isolating complexes that contain the oligonucleotides using the affinity tag to produce isolated complexes; e) enzymatically releasing the protein, RNA fragments and/or the genomic DNA fragments from the isolated complexes to produce a released component, without reversing the crosslinking; and f) analyzing the released component.

Depending on the target RNA and how the method is performed, the method may be employed to identify protein, genomic DNA and/or other cellular RNAs that interact with the target RNA, either directly or indirectly. For example, the method may be employed to identify the protein or the genome occupancy sites for a lncRNA, although other types of RNA may be investigated. For example, the method described herein may be employed to examine any type of RNA, e.g., long RNA molecules such as RNA molecules that are at least 200 nt in length as well as shorter RNAs such as scaRNAs (which are approximately 60 nt in length). Long RNA molecules include mRNA molecules, rRNA molecules and long non-coding RNA molecules (lncRNAs) such as large intergenic RNA (lincRNA) molecules. The defining characteristics of mRNA and rRNA are well known. lincRNA is relatively newly discovered, and is believed to be involved in regulating wide variety of processes, e.g, embryonic stem cell pluripotency, cell proliferation, cancer and chromatin structure. This class of molecules is reviewed by, e.g., Tingeras (Nature Biotechnology 2009 27: 346-347).

In some cases, the heat stable crosslinking agent is glutaraldehyde, although other crosslinking agents, e.g., Dimethyl Suberimidate-2 HCl or DMS, Dimethyl pimelimidate-2 HCl or DMP, Dimethyl adipimidate-2 HCl or DMA, etc., that are stable under the conditions used in the hybridization step may be employed. Crosslinkers may have a longer or shorter arm length, as desired.

In particular cases, the ribonucleotide complexes may comprise genomic DNA, in which case the genomic DNA in the complexes may be analyzed, e.g., sequenced. In other cases, the protein in the ribonucleotide complexes may be analyzed, e.g., by immunoblotting or mass spectrometry.

The sample employed may be, e.g., intact tissue culture cells, cells of a tissue (e.g., a tissue biopsy or the like), or a homogenized version of the same or a lysate of the same from any suitable tissue.

In particular methods, the fragmenting may be done enzymatically (e.g., using a restriction enzyme, DNaseI or micrococcal nuclease), chemically or mechanically, e.g., by sonication or passing through thin needles. In some cases, the fragmenting may produce fragments having an average size in the range of 100 bp to 500 bp in length, although in certain cases fragments having a size range outside of this range (e.g., 50 bp to 1,000) may be used.

In some embodiments, the oligonucleotides that are used hybridize to sites in the specific target RNA that are spaced by at least 30-100 nucleotides, e.g., 50 to 70 nt, such that, for each 1 kb of target RNA, between 5 to 20 oligonucleotides, e.g., 8-12 are used. The oligonucleotides used may in certain cases be in the range of 15 to 30 nucleotides in length, e.g., 18-25 nucleotides in length. In some cases, the oligonucleotides used are matched by G/C content (e.g., 40% to 50% GC-rich) and melting temperature (e.g., a melting temperature of at least 50° C., e.g., 55° C. to 75° C.). As such, in using the method, a target RNA may be hybridized with at least 3 (e.g., at least 3, 4, 5, 6, 7, 8, 9, or 10 or more, up to 20 oligonucleotides or more, depending on the length of the target RNA) that hybridize with the target RNA.

The target RNA to which the oligonucleotides hybridize may vary greatly. In particular cases, the oligonucleotides may hybridize to mRNA. In other cases, the oligonucleotides may hybridize to non-coding RNA, lncRNA, although other non-coding RNAs may be targeted.

The high stringency conditions used may in certain cases include an incubation at least 37° C. for at least 3 hours. The conditions used for this step should be sufficient to allow high stringency hybridization of the oligonucleotides to the RNA target, but not uncrosslinking of the sample. Formaldehyde, a commonly used crosslinking agent, is reversible under these conditions.

In particular embodiments, the oligonucleotides are biotinylated and therefore includes a biotin or biotin analog. The isolating may be done using a support (e.g., a magnetic bead or the like) that comprises a ligand for the affinity tag, e.g., streptavidin.

The releasing step may be done a variety of different ways to release depending on the component of the complexes that one wishes to analyze. For example, the components may be enzymatically released by contacting the isolated complexes with an RNAse (e.g., a cocktail of RNAseH and RNAseH; which degrades the RNA to release the protein and genomic DNA (if present) from the complex. Alternatively, components may be enzymatically released by contacting the isolated complexes with a non-specific protease (e.g., protease k; which degrades the protein to release the RNA and genomic DNA (if present) from the complex. Use of a DNAse may release the protein and RNA from the complex. The enzymes may be used in different combinations (e.g., an RNAse and a protease) to yield different components (e.g., genomic DNA). Once released, the component may be analyzed using any suitable means. For example, if the released component is genomic DNA, the genomic DNA may be sequenced (which, may, in certain cases in involving cloning or amplifying the DNA prior to sequencing). If the released component is RNA, the RNA may be sequenced (which, may, in certain cases in involving converting the RNA to cDNA prior to sequencing). Released protein may be analyzed using an antibody or by mass spectrometry, etc. Because the releasing is done enzymatically, there is no need for the complexes to be uncrosslinked prior to analysis.

The subject methods may be employed in a variety of diagnostic, drug discovery, and research applications that include, but are not limited to, diagnosis or monitoring of a disease or condition (where the profile of the interactions of an RNA provides a marker for the disease or condition), discovery of drug targets (where a particular profile is differentially present in a disease or condition and may be targeted for drug therapy), drug screening (where the effects of a drug are monitored by assessing a profile of interactions), determining drug susceptibility (where drug susceptibility is associated with a particular profile of interactions) and basic research (where is it desirable to identify the interactions with an RNA in a particular sample, or, in certain embodiments, the relative levels of a particular interactions in two or more samples).

In certain embodiments, the interaction profiles for an RNA in two or more different samples may be obtained using the above methods, and compared. In these embodiments, the results obtained from the above-described methods may be normalized, e.g., to a control RNA, and compared. This may be done by comparing ratios, or by any other means. In particular embodiments, the interaction profiles of two or more different samples may be compared to identify interactions that are associated with a particular disease or condition (e.g., an interaction that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Chromatin Isolation by RNA Purification (ChIRP) paves an additional for researchers to study interactions between long non-coding RNAs (lncRNAs) and the genome. The method has been used in flies and mammals and works well on three lncRNAs, HOTAIR, roX2 and TERC, and subcellular fractionation studies suggest that there could be numerous other chromatin-associated RNAs (caRNAs) that could be investigated. Some of these studies rely on biochemical fractionation of non-crosslinked cell lysates is can be subject to high background noise and contamination from highly abundant transcripts. In addition to the methods described above, provided herein is a highly stringent technique that involves in-vivo crosslinking of RNA-chromatin interaction, immunoprecipitation of the chromatin, e.g., using a pan-histone 3 antibody, and detection of caRNAs by quantitative RT-PCR or high-throughput sequencing. This method, which has been termed "Chromatin RNA Immunoprecipitation followed by Sequencing" (ChRIP-seq), enables researchers to identify novel caRNAs that are may be functionally implicated in imprinting, gene activation, and nascent transcript processing. Furthermore, by using antibodies against specific histone modifications, one can assign functions of caRNAs population by their association with active, enhancer, or repressive domains. The genomic targets and mechanism of action of these caRNAs can then be further explored by performing ChIRP experiments.

This method may researchers to systematically profile new lncRNAs in biological context of their interest, and provides a new tool for profiling nascent transcripts and studying RNAs involved in co-transcriptional regulation. In addition, ChRIP-ChIRP in synergy forms a full investigation pipeline that guides researchers from identification of targets through the elucidation of their mechanism of action. With minimal optimization the method could be used as a robust protocol for the study of any RNA-binding protein.

Accordingly, among other things, the instant methods may be used to link an interaction profile expression of certain genes to certain physiological events.

EXAMPLES

Materials and Methods

Cell Culture: SuperTelomerase, MDA-MB-231-HOTAIR, MDA-MB-231 HOTAIR-shEZH2 cells were maintained in DMEM (Invitrogen) supplemented with 10% FBS (HyClone) and 1% Pen/Strep (Invitrogen).

Probe Design: Morpholino Probes against HOTAIR were designed on three open regions detected by PARS-seq by Gene-Tools LLC (HOTAIR Morpho-1: GAGCAGCTCAAGTCCCCTGCATCCA (SEQ ID NO:1), HOTAIR Morpho-2: GCACCCGCTCAGGTTTTTCCAGCGT (SEQ ID NO:2), HOTAIR Morpho-3: TACATAAACCTCTGTTCTGTGAGTGC (SEQ ID NO:3), Mock Morpho: CCTCTTACCTCAGTTACAATTTATA; SEQ ID NO:4). All probes were biotinylated at the 3' end. Antisense DNA probes were designed against HOTAIR full-length sequence using online designer at www.singlemoleculefish.com. All probes were compared with the human genome using the BLAT tool and probes returning noticeable homology to non-HOTAIR targets were discarded (BLAT searches through a non-overlapping 11-mers index). 48 probes were generated and split into two sets based on their relative positions along HOTAIR sequence such as even-numbered and odd-numbered probes were separately pooled. A symmetrical set of probes against LacZ RNA was also generated as the mock control. All probes were biotinylated at the 3' end with an 18-carbon spacer arm (Protein and Nucleic Acid Facility, Stanford University). 19 probes were generated against TERC RNA and 24 for roX2 by similar methods.

Additional experiments have shown that shorter oligonucleotides may work better than longer ones. For example, 20 mers appear to have a higher signal-to-noise ratios than 50 mers, 120 mers, and 150 mers, likely because shorter oligonucleotides are less likely to be blocked by RNA structures. <20 mers, probes will likely cross-hybridize to other RNAs, therefore 20 mers are thought to be the optimal probe size. Optimal spacing of the probes appears to be about 60 bp. If probes are too densely packed there is a high chance for adjacent probes to cross-hybridize to the same piece of non-specific DNA, should there be a significant stretch of homology between the target RNA and other places in the genome. Conversely, if probes are too far apart, some fragments of the RNAs might not be captured (RNAs are sonicated to 100-500 nt pieces before ChIRP).

Crosslinking and chromatin preparation: Cells were grown to log-phase in tissue culture plates and rinsed once with room temperature PBS. For UV crosslinking, the plates were irradiated in UV crosslinker (Stratagene) with lids off and PBS aspirated. UV strength was titrated from 240 mJ to 960 mJ. For chemical crosslinking, cells were fixed on plate with appropriate amounts of 1% formaldehyde or 1% glutaraldehyde in PBS for 10 minutes at room temperature. Crosslinking was then quenched with 0.125 M glycine for 5 minutes. Cells were rinsed again with PBS, scraped into Falcon tubes, and pelleted at 800 g for formaldehyde crosslinking and 2500 g for glutaraldehyde crosslinking. Cell pellets were then snap frozen in liquid nitrogen and can be stored in −80 C indefinitely.

To prepare chromatin, cell pellets were quickly thawed in 37 C water bath and resuspended in Swelling Buffer (0.1 M Tris pH7.0, 10 mM KOAc, 15 mM MgOAc. Before use, add 1% NP-40, 1 mM DTT, 1 mM PMSF, complete protease inhibitor (GE), and 0.1 U/ul Superase-in (Ambion)) for 10' on ice. Cell suspension was then dounced and pelleted at 2500 g for 5'. Nuclei was further lysed in nuclear lysis buffer at 100 mg/ml (50 mM Tris 7.0, 10 mM EDTA, 1% SDS, add DTT, PMSF, P.I., and Superase-in before use) on ice for 10', and sonicated using Bioruptor (Diagenode) until most chromatin has solubilized and DNA is in the size range of 100-500 bp. Chromatin can be snap frozen in liquid nitrogen and stored in −80 C until use.

Hybridization and washing: Chromatin is diluted in 2 times volume of hybridization buffer (500 mM NaCl, 1% SDS, 100 mM Tris 7.0, 10 mM EDTA, 15% Formamide, add DTT, PMSF, P.I, and Superase-in fresh). 100 pmol probes were added to 3 ml of diluted chromatin, which was mixed by end-to-end rotation at 37 C for 4 hours. Streptavidin-magnetic C1 beads were washed three times in nuclear lysis buffer, blocked with 500 ng/ul yeast total RNA and 1 mg/ml BSA for 1 hour at room temperature, and washed three times again in nuclear lysis buffer before resuspended in its original volume. 100 ul washed/blocked C1 beads were added per 100 pmol of probes, and the whole reaction was mixed for another 30 min at 37 C. Beads:biotin-probes:RNA:chromatin adducts were captured by magnets (Invitrogen) and washed five times with 40× beads volume of wash buffer (2×SSC, 0.5% SDS, add DTT and PMSF fresh). After last wash buffer was removed carefully with P-10 pipette so that no trace volume was left behind. Beads are now poised for different elution protocols depending on downstream assays.

ChIRP RNA elution: For reversible crosslinking (formaldehyde), beads was resuspended in 10× original volume of RNA elution buffer (Tris 7.0, 1% SDS) and boiled for 15 min, followed by trizol:chloroform extraction and RNeasy mini column purification. For non-reversible crosslinking (UV and glutaraldehyde), beads were resuspended in 10× original volume of RNA pK buffer (100 mM NaCl, 10 mM Tris 7.0, 1 mM EDTA, 0.5% SDS) and 0.2 U/ul Proteinase K (Invitrogen). pK treatment was carried out at 65 C for 45', followed by boiling for 15', and trizol:chloroform extraction. Eluted RNA was subject to quantitative reverse-transcription PCR (QRT-PCR) for the detection of enriched transcripts.

ChIRP Protein Elution and Dot Blot: Beads were resuspended in 3× original volume of DNase buffer (100 mM NaCl and 0.1% NP-40), and protein was eluted with a cocktail of 100 ug/ml RNase A (Sigma-Aldrich) and 0.1 U/ul RNase H (Epicenter), and 100 U/ml DNase I (Invitrogen) at 37 C for 30'. Protein eluent was supplemented with 0.2 volume of 5× laemmeli buffer (without bromophenol blue or glycerol), boiled for 5', and dot blotted to nitrocellulose membrane with Bio-Dot apparatus (Biorad). Membrane was then blotted against TCAB1 and tubulin antibodies (gifts from Artandi lab) per normal Western protocol.

ChIRP DNA Elution: Beads were resuspended in 3× original volume DNA elution buffer (50 mM NaHCO$_3$, 1% SDS, 200 mM NaCl), and DNA was eluted with a cocktail of 100 ug/ml RNase A (Sigma-Aldrich) and 0.1 U/ul RNase H (Epicenter). RNase elution was carried out twice at 37 C with end-to-end rotation and eluent from both steps was combined. For formaldehyde crosslinking, chromatin was reverse-crosslinked at 65 C overnight. For non-reversible crosslinking, eluted chromatin was pK treated with 0.2 U/ul pK at 65 C for 45'. In either case, DNA was then extracted with equal volume of phenol:chloroform:isoamyl (Invitrogen) and precipitated with ethanol at −80 C overnight. Eluted DNA was subject to QPCR, Dot Blots, or high-throughput sequencing.

DNA Dot Blot: DNA was denatured in 0.1 volume of denaturing solution (4 M NaOH, 100 mM EDTA) at 95 C for 5', and then chilled on ice for 5'. Equal volume of chilled 2 M NH$_4$OAc was added to neutralize DNA on ice, which is then dot blotted onto nitrocellulose membrane using a Bio-Dot apparatus. Membrane was immediately crosslinked at 120 mJ in Stratalinker, and pre-hybridized in Rapid-Hyb (GE) at 42 C for 30'. Telomere and Alu repeats were detected using end-labeled radioactive Southern probes CCCTAACCCTAAC-CCTAACCCTAACCCTAA (SEQ ID NO:5) and GTGATC-CGCCCGCCTCGGCCTCCCAAAGTG (SEQ ID NO:6) respectively.

Deep Sequencing, Peak Calling, Motif and GO Term Analysis: High-throughput sequencing libraries were constructed from ChIRPed DNA according the ChIP-seq protocol as described (Johnson et al., 2007), and sequenced on Genome Analyzer IIx (Illumina), with read length of 36 bp. Raw reads were uniquely mapped to reference genome (hg18 assembly for HOTAIR, TERC, LacZ and EZH2 ChIRP-seq samples, and dm3 for roX2) using the Bowtie program.

ChIRP-seq workflow generally has three steps. (i) Find concordance: from the two independent ChIRP-seq experiments, we generate a consensus track, taking the lower value of the two at each coordinate. Thus, any aberrant signal in only one of the two experiments is removed. For each sample, reads from even and odd lanes were aligned separately, and per-base coverage was normalized as if there were 10 M mappable reads. For each base pair of the genome, true coverage of this base in this sample was defined as the minimum coverage of the even lane and odd lane.

$$\text{ture\_coverage\_of\_base}_i = \min(\text{even\_coverage}_i, \text{odd\_coverage}_i)$$

Genome wide signal consists of a combine lane, based on which, a SAM file was generated for peak calling. (ii) Find peaks: Peaks of each sample were called using the MACS program against its corresponding input with p-value cutoff 1e-5. (iii) Filter peaks: For each MACS peak, we filter for peaks that share the same shape in the raw data from the two independent experiments. Only peaks with substantial correlation of the raw data profile, and high coverage across the peak are accepted. For each MACS predicted peak, a window size of +/−2 kbp around peak summit or peak width, whichever is smaller, is selected. Within this window, an average coverage of the combine lane and a Pearson correlation between the normalized per-base coverage of the even lane and odd lane were calculated. MACS predicted peaks were further filtered based on peak length, fold enriched against input lane, average coverage, and Pearson correlation to obtain a list of true peaks. For HOTAIR ChIRP-seq sample, thresholds of average coverage>1.5, Pearson correlation>0.3, and fold enrichment against input>2 were applied to filter MACS predicted peaks and obtained 832 true peaks. Same thresholds were used to obtain 2198 true TERC peaks. For roX2 ChIRP-seq, similar parameters were used with the additional cut-off of peak length >2300 bp, based on the fact that roX2/MSL complexes cover entire genes. 308 true peaks were obtained.

Sequences of top 500 true peaks (ranked by fold enrichment) within +/−200 bp around peak summits were extracted and motifs analysis against these 500 peaks was performed using MEME. Only motifs of the highest significance were reported. Enriched gene sets were obtained through GREAT on all 2198 TERC true peaks and all 832 HOTAIR true peaks. Gene Ontology of both gene sets were performed using DAVID.

roX2 ChIRP-seq Analysis: roX2 peaks and motif were obtained in a way described above, within 308 predicted true peaks, none was in autosomes, resulted a false discovery rate (FDR)=0. Normalized signal of both the combine lane of Rox2 ChIRP-seq and MSL3-TAP ChIP-seq was obtained in a similar way described in HOTAIR ChIRP-seq analysis. Only regions where normalized signal is >=10 were counted in calculating the Pearson correlation between Rox2 and MSL3-TAP samples. Genes who overlaps >=1 bp with windows +/−2 kbp of true Rox2 peak summits were included in the average diagram. In total, 1087 RefSeq transcripts were included in chrX average diagram, and 4260 RefSeq transcripts were included in that of chr2L. Distance on the diagram was scaled with gene length, so that the diagram shows signal in a region from 50% gene length upstream to 50% gene length downstream.

TERC ChIRP-seq Analysis: Reads from "TERC ChIRP" sample and "Input" sample were compared against telomere sequence (CCCTAAx5; SEQ ID NO:5) and Alu sequence (GTGATCCGCCCGCCTCGGCCTCCCAAAGTG; SEQ ID NO:6). Complete matches were tallied and divided by total number of reads in that sample to give Reads per Million (RPM). RPMs from TERC enriched sample were divided with those from the Input sample to give "Fold Enrichment."

HOTAIR ChIRP-seq Analysis: Normalized signal within 10 kb upstream and downstream of the summits of true HOTAIR peaks were extracted with a smooth window size of 50 bp. Within each 50 bp, the normalized HOTAIR ChIRP signal is calculated via:

$$\text{normalized\_signal} = \log_2\left(\sum_{i=1}^{50} \frac{\text{true\_coverage\_of\_}base_i}{\text{number\_of\_unique\_mappable\_reads}} \times 10,000,000\right)$$

Suz12, Ezh2 and H3K27Me3 ChIP-chip data were generated previous by others. ChIP-chip signal of Suz12, Ezh2 and H3K27Me3 of 10 kb upstream and downstream of HOTAIR peak summits were also extracted in a similar way.

RESULTS

Example 1

Development and Optimization of ChIRP

A new method, referred to herein as "ChIRP" that allows unbiased high-throughput discovery of RNA-bound DNA, RNA and proteins is provided (FIG. 1A). In this example, cultured cells are crosslinked in vivo, and their chromatin extracted and homogenized. Biotinylated complementary oligonucleotides that tile the RNA of interest were hybridized to target RNAs, and isolated using magnetic streptavidin beads. Co-purified chromatin was eluted for protein, RNA, or DNA, which was then subject to downstream assays for identification and quantitation.

Figure 7:
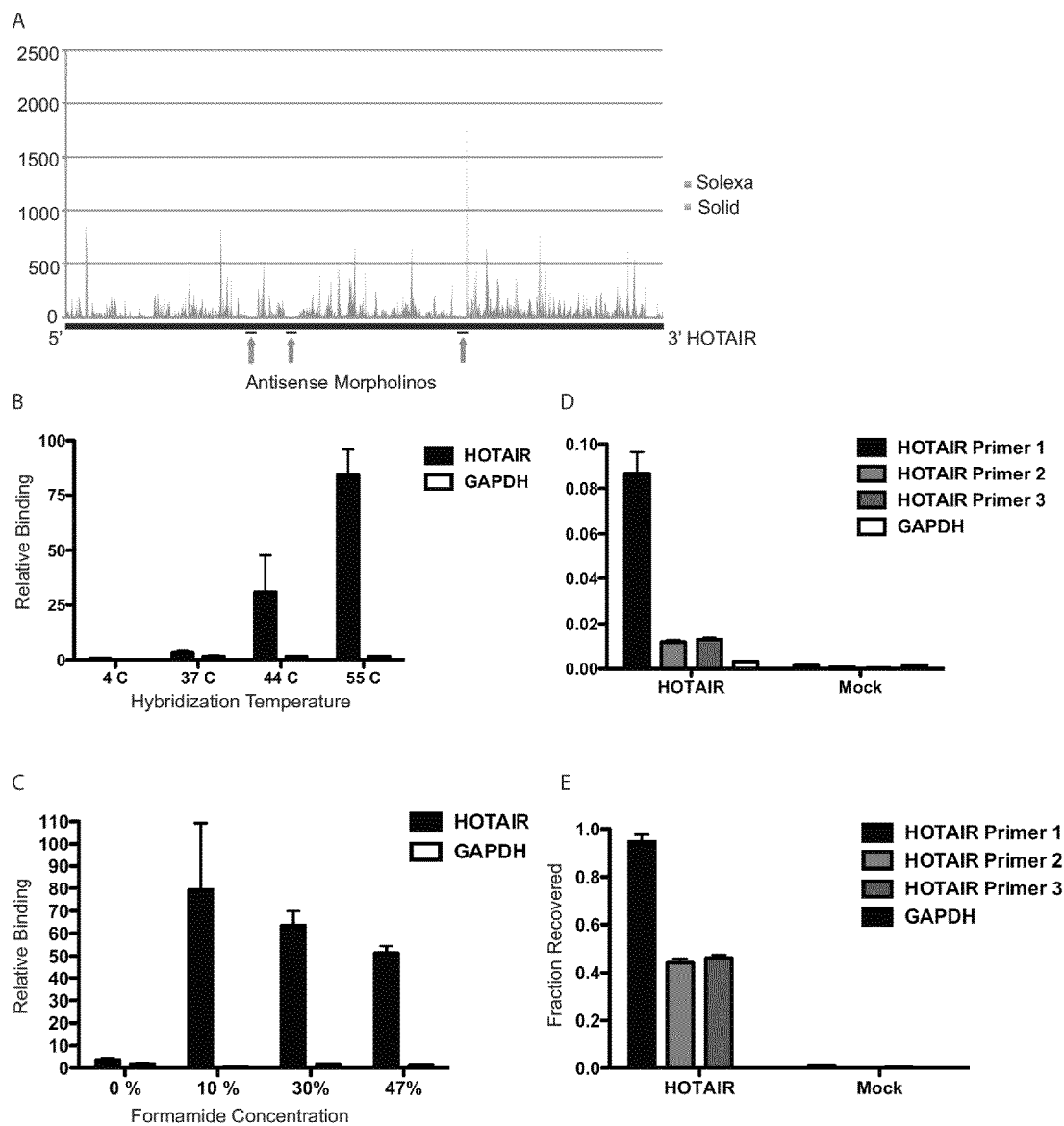
FIG. 7(A) Three antisense morpholinos are designed against structurally open regions of HOTAIR RNA. Peaks denote secondary structures previously determined by Parallel Analysis of RNA Structure (PARS) (Kertesz et. al., 2010). (B) Higher hybridization temperatures confer better ChIRP stringency. (C) A moderate formamide concentration (10%) achieves good ChIRP strigency at the mild temperature of 37 C. (D) ChIRP efficiency measured by HOTAIR primers targeting different regions of the transcript. 3-Morpholino strategy gives low yield (9% retrieval at best) and high positional bias (~10 fold difference across primers). (E) Tiling probes obtain high yield (50-95% retrieval, note the difference in the scale of Y-axis from (D)) and smaller positional bias (<2 fold across primers).

This example uses multiple non-overlapping oligonucleotides per target sequence. Initial attempts to capture a lncRNA with morpholino probes, which are high-affinity ribonucleotide analogues resistant to nuclease digestion. As lncRNAs are known to be highly structured, three morpholino probes were designed against single-stranded portions of HOTAIR, as determined by prior high-throughput RNA secondary structure measurements (FIG. 7A). As a negative control a morpholino probe that bore no sequence homology with any human RNA was synthesized. A wide array of hybridization parameters were titrated, and consistently obtained best results under high ionic strength and higher hybridization temperature (FIG. 7B) and moderately denaturing conditions (FIG. 7C). However, with the 3-probe approach we could retrieve at most ~10% of HOTAIR RNA (FIG. 7C). Importantly, the HOTAIR transcript was sheared into the size range of ~100 nt to 500 nt during sonication, a step necessary for the solubilization of chromatin (FIG. 1B). The 3-oligo approach was possibly ineffective at recovering all fragments of long RNAs such as HOTAIR, and indeed qRT-PCR primers targeting distinct regions of HOTAIR reported drastically different efficiencies of recovery from the same pull down (~10 fold range, FIG. 7D). This raised a potential concern because functional domains of HOTAIR at its 5' and 3' ends could potentially be lost due to their distance away from arbitrarily chosen probes. Moreover, without prior knowledge of the DNA interacting domain within a lncRNA, it may be difficult to decide where to target a small number of oligonucleotide probes or insert a RNA aptamer to consistently retrieve a lncRNA of interest on chromatin.

To develop a method that is applicable to any lncRNA without prior knowledge of its secondary structure or functional domains, all parts of HOTAIR were targeted equally. Thus, 48 complementary DNA oligonucleotides that were 20 mer each and tiled the entire length of HOTAIR across 2.2 kb (~50% tiled) were designed (FIG. 1C). Sequences that have extensive complementarity to other sites in the genome or are repetitive are excluded (Methods). As a negative control, we designed a similar set of probes that targeted the LacZ mRNA, normally absent from human cells. With the tiling probes, we could pull down almost all HOTAIR RNA from chromatin (FIG. 1D), a substantial improvement over the 3-morpholinos approach. HOTAIR probes did not retrieve GAPDH nor did LacZ probes retrieve HOTAIR (FIG. 1D), demonstrating the specificity of the method. Furthermore, HOTAIR fragments were equally recovered (<2-fold difference between different qRT-PCR primers, FIG. 7E), further demonstrating the strength of a non-biased targeting method.

Figure 2:
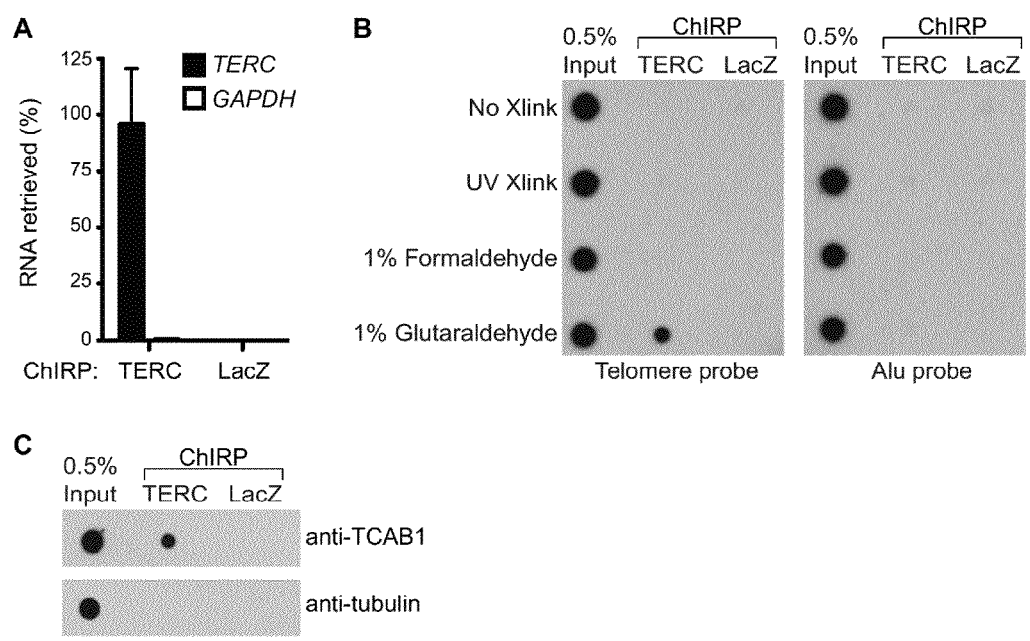
FIG. 2 ChIRP enriches for TERC RNA and detects TERC-associated telomere DNA and TCAB 1 protein. (A) TERC-asDNA probes retrieve ~88% of cellular TERC RNA and undetectable GAPDH. LacZ-asDNA probes retrieve neither RNAs. (B) Effect of different crosslinking agents on ChIRP-southern. After 1% glutaraldehyde crosslinking, TERC retrieval co-purifies telomeric repeats, but not Alu repeats. (C) TERC ChIRP retrieves TCAB1, a known telomerase holocomplex chaperone proteins. As a negative control tubulin was not detected.

Whether lncRNA-associated DNA and proteins could be co-purified was tested. As a positive control, the TERC RNA was examined, which functions as the template and scaffold for the telomerase complex. In HeLa S3 cells transduced with human TERC and TERT, TERC RNA expression is ~4 fold over control and constitutively bound at telomeric ends of dividing chromosomes. Using 19 probes complementary DNA against TERC RNA (84% tiled) or LacZ, ~90% of total TERC RNA was specifically retrieved (FIG. 2A), showing that the method is easily compatible with other lncRNAs. The DNA was eluted off of beads using a combination of RNase A and RNase H so that only DNA retrieved via a RNA bridge, but not direct probe-DNA interaction, could be preferentially released. Various crosslinking strategies for fixing RNA:DNA:protein interactions were evaluated. Consistent with classic electron micrographs showing RNA at chromatin using the thermo-stable crosslinker glutaraldehyde, it was found that glutaraldehyde crosslinking consistently yielded the highest signal-to-noise ratio in comparison to ultraviolet light or formaldehyde crosslinking (FIG. 2B). TERC ChIRP specifically retrieved telomere DNA but not Alu repeats, while LacZ ChIRP retrieved neither (FIG. 2B). The telomere ChIRP signal could not have arisen due to direct probe-telomere interaction: The CCCTAA template region on TERC was avoided in probe design (for this reason), and no probe shared homology with telomeric sequences. Furthermore, the ChIRP signal was crosslinking-dependent, suggesting that it was specific to telomere-TERC interaction. As another positive control for the method, we found that TERC ChIRP specifically retrieved TCAB1, a subunit of the telomerase holoenzyme that facilitates telomerase trafficking (FIG. 2C). Thus, ChIRP is compatible with the simultaneous analysis of DNA and proteins associated with specific RNAs.

Figure 8:
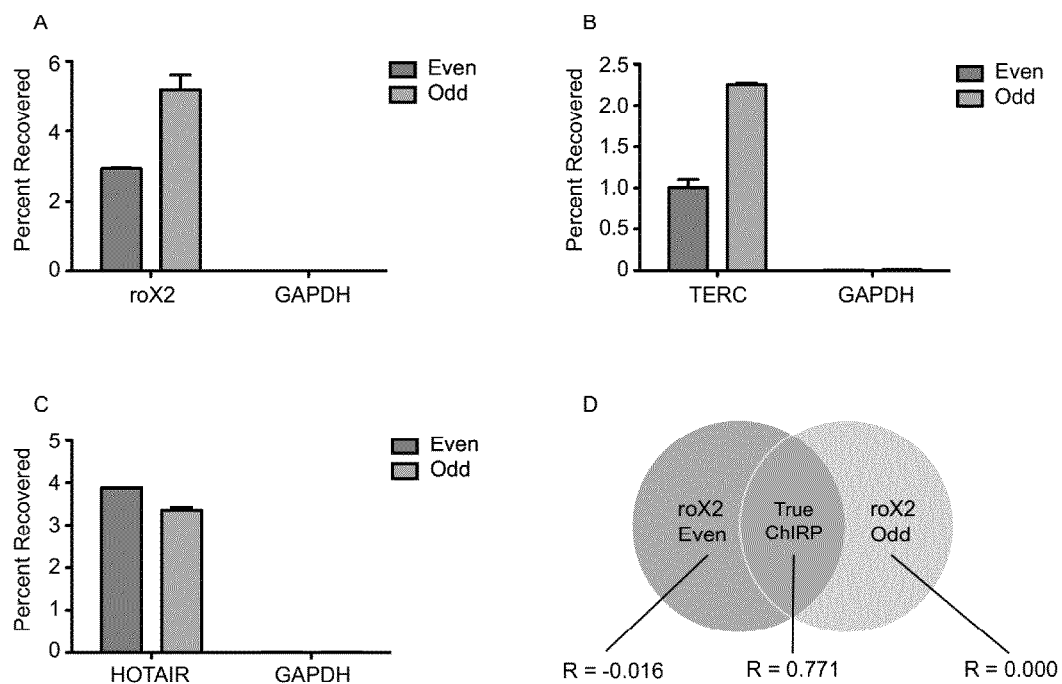
FIG. 8(A) (B) (C) "Even" and "odd" probes retrieve comparable amounts of (A) roX2, (B) TERC and (C) HOTAIR. (D) roX2 "even" or "odd" alone has little correlation with MSL3 ChIP-seq results. Their overlap, however, correlates significantly with MSL3 ChIP-seq.

One potential source of noise in ChIRP-seq is the precipitation of non-specific DNA fragments from off-target hybridization of the pool of oligonucleotide probes. In order to eliminate such potential artifacts, a "split-probe" strategy was devised, all probes were ranked based on their relative positions along the target RNA, and then split into two pools such that all even probes were in one set and all odd probes in another. As the two sets of probes shared no overlapping sequences, the only target they have in common is the RNA of interest and its associated chromatin. Similar to using two independent polyclonal antibodies to obtain high confidence ChIP-seq signal, two independent ChIRP-seq runs were performed with "even" and "odd" probes separately. The analysis was focused exclusively on the overlap between their signals. Notably, "even" and "odd" probe sets enriched each of the target RNA below with similar efficiency, yielding comparable ChIRP-seq libraries in terms of signal-to-noise ratio (FIG. 8).

Example 2

ChIRP-seq Elucidates roX2 Binding Sites on X Chromosome

To assess the sensitivity and specificity of ChIRP when applied genome-wide, a biological system was used in which the binding sites of a lincRNA are already known genome-wide, and in which ChIRP-seq selectively retrieves most of these sites. The *Drosophila* dosage compensation system is ideal for this purpose. In *Drosophila*, male cells up-regulate the expression of genes on their single X chromosome by two-fold; this dosage compensation requires a ribonucleoprotein complex containing the Male-Specific Lethal (MSL) proteins and two lncRNAs, roX1 and roX2. Staining of polytene chromosomes showed that roX and MSL co-localize exclusively on the male X chromosome but not on autosomes, and pioneering work by Kuroda and colleagues have defined the occupancy landscape of MSL proteins at high resolution.

Figure 3:
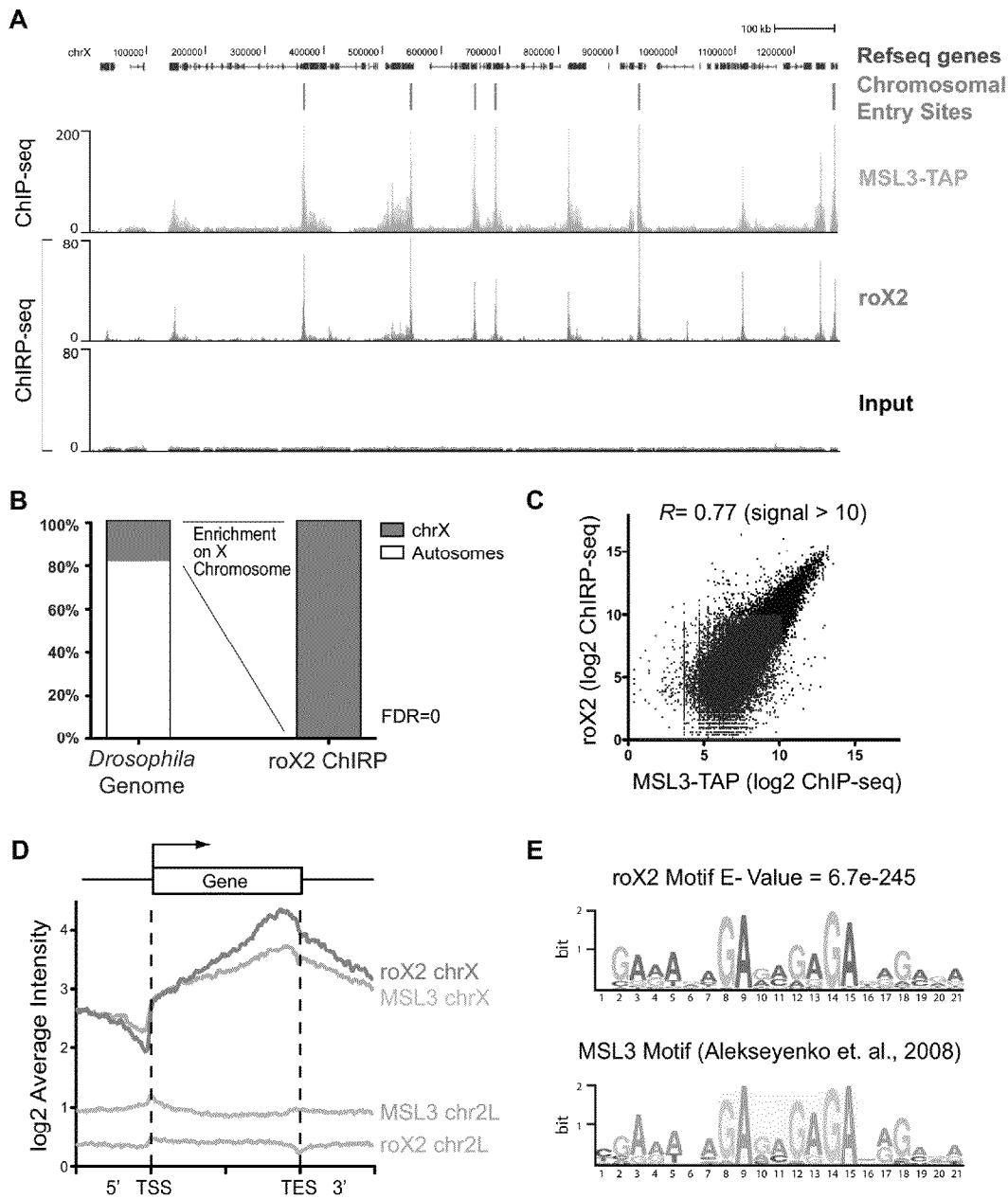
FIG. 3 ChIRP-seq reveals roX2 binding sites on X chromosome. (A) roX2 co-localizes with MSL complex and CES. (B) 308 roX2 binding sites are all on the X chromosome, indicating an FDR~0. (C) roX2 ChIRP-seq is overall highly correlated to MSL3 ChIP-seq (R=0.77 for $\log_2$ intensity>10). (D) roX2 binds across X-linked gene bodies with bias towards the 3' end, in a manner similar to MSL3 but with higher dynamic range. ChIRP-seq or ChIP-seq signal intensity for all bound genes on X or genes on chromosome 2 L were averaged and to gene start and end annotations. (E) roX2 binding sites are strongly enriched for a sequence motif that is nearly identical to MSL3 motif.

ChIRP-seq was performed on endogenous roX2 in male S2 cells. Using the software MACS, we identified 308 roX2 binding sites—all of them are on the X chromosome and none on autosomes (FIG. 3A, B). Autosomes constitute ~80% of the *Drosophila* genome. Thus, ChIRP-seq is highly specific even on a genome-wide scale, and has a negligible false discovery rate (FDR~0). The 308 rox2 binding sites recovered 89.3% of known Chromosomal Entry Sites (CES), which are high affinity binding sites of the roX-MSL complex that have been previously defined by genetic epistasis. This number compares favorably with ChIP-seq of single MSL components, whose top 309 peaks identified 91% of CES. roX2 ChIRP-seq profile is highly correlated with MSL ChIP-seq profile, and both show very strong peaks at CES (FIG. 3A). The roX2 and MSL occupancy profiles show a Pearson correlation of 0.77, which is in the range of correlation for biological replicates of a single MSL protein, or ChIP-seq of different MSL subunits in parallel (FIG. 3A, C; R=0.65-0.94). Remarkably, direct comparison of roX2 ChIRP-seq vs. MSL3 ChIP-seq shows that ChIRP-seq has better dynamic range and discrimination of X chromosome vs. autosomes than ChIP-seq (FIG. 3D). Aligning roX2 ChIRP signal across all bound genes, we discovered that the roX2 occupancy is enriched over gene bodies of X chromosome genes, and increases from 5' to 3' end of each gene. This pattern provides independent support for a recent notion that the roX-MSL complex acts by promoting transcriptional elongation rather than initiation (FIG. 3D). In addition, motif analysis of roX2 ChIRP-seq data revealed a very significantly enriched DNA motif that is nearly identical to the MSL motif (a sequence shown to function as CES when inserted into autosomes) (FIG. 3E). These data demonstrate that ChIRP-seq is highly sensitive and specific, and retrieves biologically useful signal.

Consistent with the hypothesis that the shared signal between even and odd probes will improve ChIRP-seq accuracy, it was found that the shared signal between the two independent probe sets are highly correlated with that of MSL3 ChIP-seq while the unique signals in either probe sets alone were not (FIG. 8D). Based on these findings, at least two ChIRP-seq experiments were performed using independent sets of non-overlapping probes for each target RNAs, and we only accept binding sites that are concordant in both experiments. In certain cases, only the shared signal between from two independent ChIRP-seq experiments can be considered meaningful signal and signal present in only even or odd experiments alone should not be interpreted.

Example 3

ChIRP-seq Reveals TERC Occupancy Sites Genome-Wide

Figure 4:
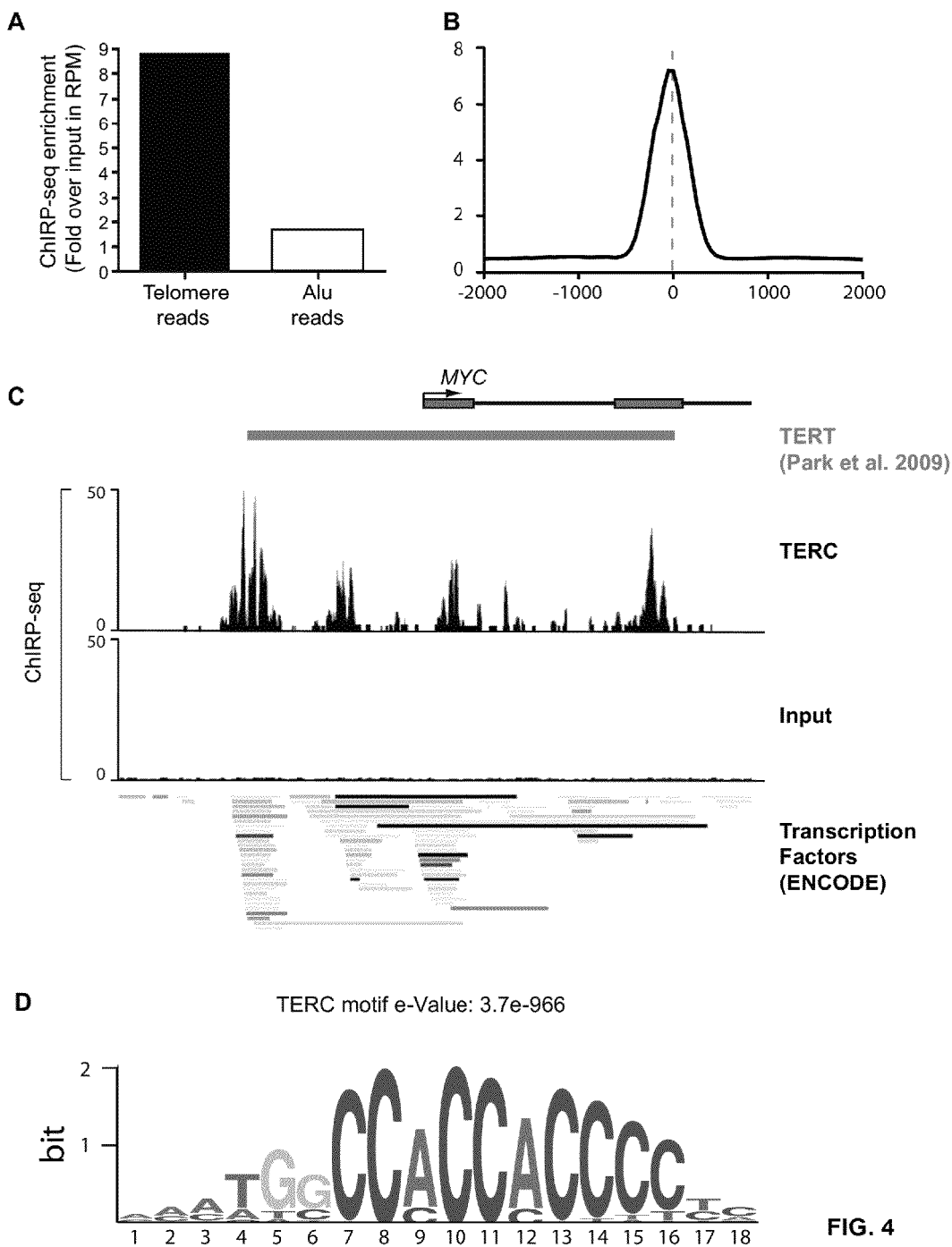
FIG. 4 TERC ChIRP-seq. (A) Fold enrichment of reads from TERC-ChIRP-seq and Input sample that map to telomere and Alu sequences. (B) TERC peaks are focal. (C) TERC occupancy at the MYC promoter, overlaying regions of TERT occupancy (Park et. al., 2009) and regions of dense transcription factors occupancy identified by the ENCODE project (bottom). (D) A cytosine-rich motif enriched among TERC-binding sites (e-Value=3.7e-966).

ChIRP-seq of TERC in HeLa S3 cells transduced with TERT and TERC was performed. TERC ChIRP-seq showed significant enrichment of telomeric DNA sequences (~9 fold) relative to input reads, whereas Alu repeats were not (FIG. 4A). In addition, numerous specific TERC binding events were observed throughout the genome with signal intensities comparable to conventional ChIP-seq. TERC binding sites were focal; most binding sites are "peaks" of <600 bp that do not spread beyond 1 kb (FIG. 4B), which is a pattern reminiscent of ChIP-seq peaks of transcription factors.

Using the same analysis pipeline employed in roX2 analysis, over 2198 TERC binding sites in the genome were identified, which represents a large resource to study potential non-canonical functions of TERC RNA and telomerase. It is known that TERT can bind to and co-activate Wnt target genes at chromatin, and it was hypothesized that TERC, as a component of the TERT complex, may also co-occupy some of the same genes. Unbiased analysis of the TERC-bound peaks revealed that one of the top three enriched Gene Ontology terms is Wnt receptor signaling pathway ($p=1.3\times10^{-6}$), strongly supporting the initial hypothesis. It was found that TERC occupied multiple Wnt genes directly, including WNT11, which is transcriptionally induced by TERT overexpression in vivo. ChIRP-seq revealed a series of TERC binding peaks near the MYC gene, concordant with previously documented binding sites of TERT (FIG. 4C). Analysis of TERC-bound sequences identified an enriched cytosine rich sequence motif (FIG. 4D), suggesting that specific DNA motifs may be involved in TERC occupancy. These results bolster the concept of direct connections between chromosome replication and self-renewal pathways.

Example 4

ChIRP-seq Reveals HOTAIR Nucleation of Polycomb Domains

The genomic binding sites of HOTAIR and their relationship with Polycomb occupancy were investigated. HOTAIR is a 2.2 kb lincRNA from the HOXC locus that binds the Polycomb Repressive Complex 2 (PRC2) and affects PRC2 occupancy to target genes throughout the genome. How HOTAIR guides PRC2 to target genes is not understood. Overexpression of HOTAIR alters the positional identity of cancer cells and promotes cancer metastasis. HOTAIR occupancy was mapped genome-wide by ChIRP-seq in MDA-MB-231 breast cancer cells expressing HOTAIR, which matches the HOTAIR level and phenotypic consequences in metastasis-prone human breast cancers.

Figure 5:
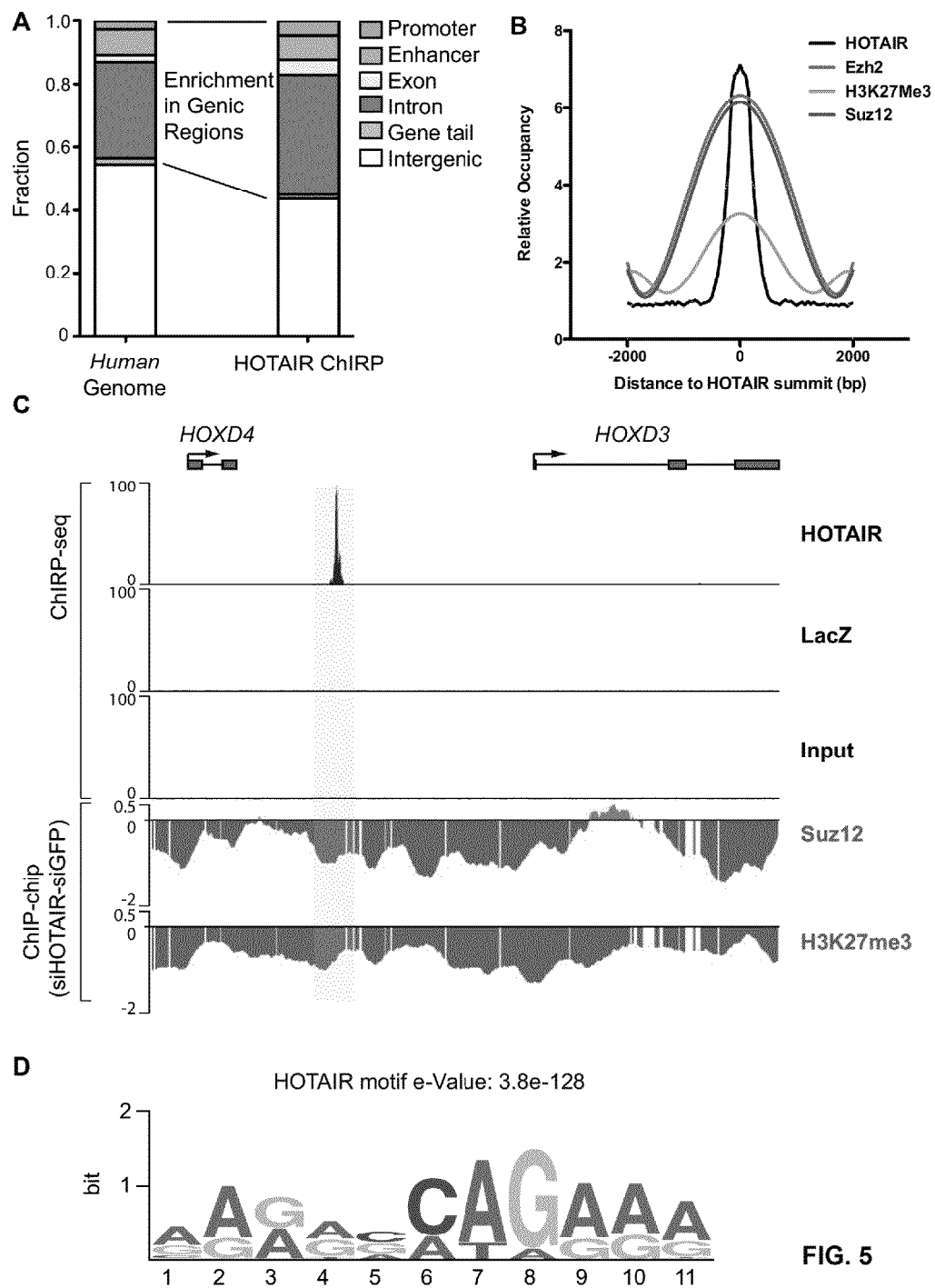
FIG. 5 HOTAIR ChIRP-seq suggests mechanisms of HOTAIR-recruitment of PRC2. (A) HOTAIR binding sites are enriched in genic regions, notably enhancers and introns. (B) Metagene analysis of genomic regions aligned by 832 HOTAIR ChIRP peaks show focal HOTAIR peaks in association with broad domains PRC2 occupancy (evidenced by subunits EZH2 and Suz12) and H3K27Me3. (C) HOTAIR nucleates broad domains of PRC2 occupancy. A HOTAIR binding site between HOXD3 and HOXD4 lies in the center of a broad domain of Suz12 and H3K27Me3 occupancy that are both lost upon HOTAIR knock down (Tsai et. al., 2010, Rinn et. al., 2007). (D) GA-rich homopurine motif enriched in HOTAIR binding sites.

832 HOTAIR occupancy sites were identified genome-wide, using the same analysis pipeline described above with two independent ChIRP-seq probe sets. HOTAIR binding sites occur on multiple chromosomes and are enriched in genic regions, notably regions annotated as enhancers and introns (FIG. 5A). HOTAIR binding events are focal; typical HOTAIR peaks are no more than a few hundred base pairs, a pattern reminiscent of transcription factors. When overlaid with previous generated genomic-binding data of PRC2 subunits EZH2, SUZ12, and H3K27Me3 in the same cell type, a significant pattern of co-occupancy was identified (FIG. 5B). Focal sites of HOTAIR occupancy are associated with more broad domains of PRC2 occupancy and H3K27me3, suggesting that HOTAIR may nucleate Polycomb domains. One prime example of this pattern is in the human HOXD locus, where HOTAIR is known to target PRC2 to silence multiple HOXD genes across 40 kilobases. One of the high confidence HOTAIR ChIRP-seq peaks mapped to the intergenic region between HOXD3 and HOXD4, which corresponds to middle of a broad domain of H3K27me3 and SUZ12 occupancy loss upon HOTAIR depletion (FIG. 5C). HOTAIR occupancy sites are significantly enriched for genes that gain PRC2 occupancy in a HOTAIR-dependent manner in the same cell type, or become de-repressed when endogenous HOTAIR is depleted (Gupta et al., 2010; Tsai et al., 2010) ($p=2.4 \times 10^{-5}$ and $p=8.57 \times 10^{-3}$ respectively, hypergeometric distribution). Unbiased analyses of HOTAIR occupied genes revealed enrichment for genes involved in pattern specification processes ($p=8.7 \times 10^{-7}$), consistent with prior data that HOTAIR enforces the epigenomic state of distal and posterior positional identity. These results provide additional evidence that HOTAIR-chromatin interaction is associated with PRC2 relocalization and gene silencing. Despite these significant overlaps, it is clear that the correspondence between HOTAIR occupancy and downstream effects (PRC2 occupancy, gene silencing) does not map one-to-one, which may suggest additional layers of complexity.

ChIRP-seq data enable potentially new mechanistic insights into RNA-chromatin interaction. Analysis of HOTAIR binding sites revealed enrichment of a GA-rich polypurine motif ($e=3.8$ e–128, FIG. 5D), which we term the HOTAIR motif. Interestingly, Drosphila Polycomb Response Element (PRE) are known to bind GAGA protein, and recent studies of mammalian PREs also identified GA-repeats as a shared feature, although other sequences are also required. In addition, the MSL/roX ribonucleoprotein complex responsible for dosage compensation in Drosophila also recognizes a GA-rich element on fly X chromosome, raising the intriguing possibility of similar mechanisms where lncRNAs could potentially serve as guides for chromatin-lncRNA complexes such as PRC2-HOTAIR and MSL-roX.

Example 5

HOTAIR Occupancy Occurs Independent of EZH2

Figure 6:
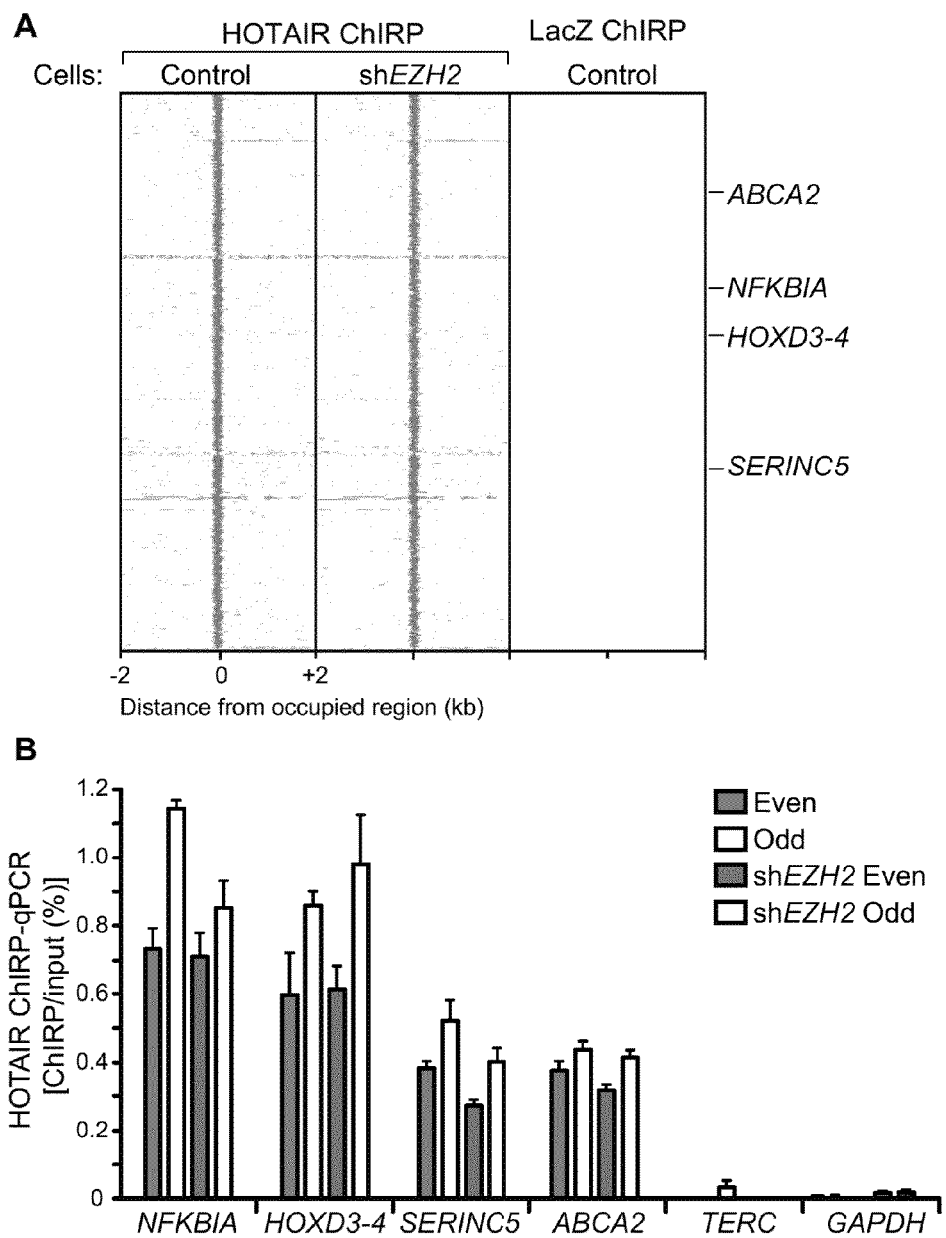
FIG. 6(A) HOTAIR binds chromatin in a PRC2-independent manner. Each row is a 4 kB genomic window centered on a HOTAIR ChIRP peak in control cells; the peaks are aligned for the 832 HOTAIR bound sites (left panel). Red color intensity indicates the number of ChIRP-seq reads. The equivalent genomic windows in control and shEZH2 cells show that LacZ ChIRP retrieved no signal (right panel) while shEZH2 did not diminish or alter the profile of HOTAIR occupancy (middle panel). (B) ChIRP-qPCR validation of peaks from (A). TERC and GAPDH served as negative controls. Mean+ s.d. are shown.

HOTAIR may actively recruit PRC2 to it targets genes, or simply serve as a scaffolding molecule that gets passively transported along with PRC2. The observed pattern of focal HOTAIR occupancy in the midst of broader domains of PRC2 strongly suggests the former hypothesis. To formally distinguish between these two possibilities, we performed HOTAIR ChIRP-seq in isogenic cells depleted for EZH2, which directly binds HOTAIR. Notably, the pattern of HOTAIR occupancy was largely preserved upon EZH2 depletion (FIG. 6A), indicating that HOTAIR can bind chromatin without an intact PRC2. Independent ChIRP-qPCR validated the binding sites and confirmed the specificity of ChIRP-seq results in control and shEZH2 cells (FIG. 6B). Together, these results support the role HOTAIR lincRNA as an active recruiter of chromatin modifying complexes.

Discussion of Examples 1-5

ChIRP-seq, a new method of mapping in vivo RNA binding sites genome-wide, is described. Some parameters used were use of split pools of tiling oligonucleotide probes and glutaraldehyde crosslinking. The design of affinity-probes is straightforward given the RNA sequence and requires no prior knowledge of the RNA's structure or functional domains. Our success with roX2, TERC, and HOTAIR—three rather different RNAs in two species—suggests that ChIRP-seq is likely generalizable to other RNAs, particularly lncRNAs. As with all experiments, care and proper controls are required to interpret the results. Different RNAs may require titration of conditions, and judicious change of conditions, such as selection of different affinity probes or crosslinkers, may highlight different aspects of RNA-chromatin interactions. Like ChIP-seq, not all binding events are necessarily functional, and additional studies are required to ascertain the biological consequences of RNA occupancy on chromatin. Nonetheless, we foresee many interesting application of this technology for researchers of other chromatin-associated lncRNAs, which number now in the thousands. Just as ChIP-seq has opened the door for genome-wide explorations of DNA-protein interactions, ChIRP-seq studies of the "RNA interactome" may reveal many new avenues of biology.

ChIRP-seq has enabled the first genome-wide views of ncRNA occupancy on the human genome. Commonalities in the occupancy patterns of TERC and HOTAIR suggest several lessons for RNA-chromatin interactions. First, lincRNA binding sites are focal, specific, and numerous. In contrast to histone modifications which often broadly occupy certain genomic elements (e.g. promoters, enhancers, transcribed exons, or silent genes, the focal, interspersed, and gene-selective nature of lincRNA occupancy more resembles transcription factors. Even roX2, which binds across gene bodies of fly X-linked genes, shows focal peaks of high occupancy at CES sites. These results imply that certain lincRNAs may be "selector" elements that can access the genome in a highly discriminating fashion.

Second, lincRNAs access the genome through specific DNA sequences. Using ChIRP-seq, it was shown that genome-scale collections of RNA binding sites can be used to discover the enriched underlying DNA sequence motifs. These findings indicate the existence of an entirely new class of regulatory elements—lincRNA target sites—in the genome. For instance, it was discovered a GA-rich homopurine motif for HOTAIR, a lincRNA known to recruit Polycomb. Importantly, mammalian Polycomb response elements are known to have a GAGA motif, but the cognate partner has been lacking. The HOTAIR motif also has similarities to the MSL binding motif in that both are GA-rich. But the HOTAIR motif is more degenerate than the MSL motif and does not strictly conserve a GAGA sequence. The discovery of specific RNA targeting motifs may start to unify at a mechanistic level many of the disparate phenomena that involve RNA-mediated chromatin states. The GA-rich HOTAIR motif may enable formation of RNA:DNA:DNA triplex (facilitated by homopurine runs and known mediate some lncRNA-chromatin interaction, serve as the binding site of a protein that recruits HOTAIR, or indirectly configure a chromatin state that facilitates HOTAIR binding. Additional studies are required to evaluate these hypotheses, which are now possible due to ChIRP and knowledge of the candidate motif. HOTAIR also binds the LSD1-coREST-REST complex that can target DNA, and multiple mechanisms may operate together to target lincRNAs.

Third, comparison of lincRNA occupancy map with chromatin state maps can reveal the order and logic of the regulatory cascade. For instance, comparison of HOTAIR versus Polycomb occupancy suggested that HOTAIR nucleates Polycomb domains. Focal HOTAIR binding sites (<500 bp) occur in the midst of a broad domain of Polycomb that can extend in both directions for several kilobases. This pattern argues that HOTAIR does not simply bind to or stabilize pre-existing Polycomb, which would have predicted broad co-occupancy of the two. Rather, the maps suggested that the RNA may be a pioneering factor that recruits Polycomb, which then spreads out bilaterally. To directly test the order of occupancy, we depleted PRC2 subunit EZH2 and showed that HOTAIR can bind to target chromatin genome-wide. This result uncouples the formation of HOTAIR-PRC2 ribonucleoprotein complex (the RNA scaffold function) from RNA targeting to chromatin. Because EZH2 is the enzymatic subunit of PRC2, H3K27me3 is also presumably not required a priori for HOTAIR targeting. Thus, the information for target gene selectivity resides in the RNA, which then recruits Polycomb to chromatin. Prior efforts have identified sequence motifs associated with PRC2 occupancy as a function of HOTAIR, which may facilitate the spreading of PRC2 occupancy. It was previously shown that EZH2 depletion diminished the metastatic potential of HOTAIR-expression cancer cells. The ChIRP-seq data indicate that it is the lack of PRC2, rather than the inactivation of HOTAIR function at chromatin, that is responsible for this epistatic interaction. Together, these experiments suggest that lincRNAs are surprisingly like sequence-specific transcription factors in dictating chromatin states, and again suggests the utility of ChIRP to generate mechanistic insights.

Example 6

ChRIP Methodology

Briefly, chromatin-RNA interactions are fixed in-vivo by glutaraldehyde cros slinking on cells. Cells are harvested and stored at −80 C indefinitely or immediately lysed. The lysate is solubilized by sonication, and chromatin was immuno precipitated by antibodies specific towards histone 3 or histone tail modifications (e.g. H3 lysine 4 trimethylation). Chromatin-bound RNAs are retrieved by proteinase K treatment of eluent and trizol extraction. These RNAs are converted into next-gen sequencing libraries using the Ovation-V2 kit (Nugen, C.A.) or directly measured by quantitative RT-PCR.

A detailed protocol is set forth below.

1) Cell Harvesting
   Grow cells to log phase
   Trypsinize and pool 40 million cells per 50 ml falcon tube
   Wash with 40 ml of cold PBS once
   Make fresh 1% glutaraldehyde in room temperature PBS from 25% stock, discard remaining stock
   Resuspend cell pellet in 1 ml of glutaraldehyde solution and use a p1000 pipette to resuspend well
   top up to 40 ml (1 ml % glutaraldehyde/1 million cells)
   invert a couple times, shake gently for 10 min
   quench with 1/10 volume of 1.25 M glycine
   invert a couple times, shake gently for 5 min
   spin down 2000 g, 4 min
   wash pellet once with 40 ml cold PBS
   resuspend pellet in 1 ml/20 million cells of cold PBS
   aliquot 1 ml to each fresh eppendorf tube
   spin down 2000 g, 4 min
   aspirate carefully, flash freeze cell pellets, store at −80 C 2) Sonication
   Thaw cell pellet in hand and spin down 2000 g 4 min
   remove any remaining PBS
   lyse cells in 1ml of lysis buffer per 20 million cells
   sonicate till chromatin size is ~300-2000 bp and lysate is clear
   spin down lysate at 16000 g for 10 min
   flash freeze the supernant and store in −80 C 3) ChRIP
   Thaw chromatin, aliquot 200 ul (4 million cells) per reaction
   add 400 ul dilution buffer to each reaction
   add 5 ug of H3 antibody or IgG control antibody to each reaction
   shake end-to-end at 4 C overnight
   Next day: Use 50 ul Protein A dynabeads per 5 ug antibody IP
   Wash beads with 5 times original volume of dilution buffer 4 times
   Do not exceed 200 ul original volume of beads per tube
   At last wash, aliquot beads to 1 tube per reaction
   Aspirate buffer, resuspend and transfer beads to your IP using 200 ul of the IP sample
   End to end shake at room temperature for 2 hours
   Wash with 1 ml wash buffer 4 times
   resuspend beads in 50 ul IP elution buffer, vortex at setting 1 for 15 min
   transfer supernatant to a fresh tube. Repeat elution on beads for once more
   combine supernatant for a total of 100 uL. Immediatley add 5 uL 3 M NaOAc to neutralize pH
   Add 10 ul TurboDnase buffer and 1 ul TurboDnase (Ambion), 37 C for 30 min
   Add 5 ul Proteinase K (Ambion), 50 C 45 min
   Add 1 ml Trizol, extract RNA using your preferred protocol (we use miRNeasy mini column)
   Dnase treat the RNA again to completely kill residual RNA
   qRT-PCR to check for RNA enrichment
Buffers:
   Lysis Buffer:
   1% SDS
   50 mM Tris 7.0
   10 mM EDTA Dilution Buffer:
0.01% SDS
1.1% Triton X 100
1.2 mM EDTA
16.7 mM Tris 7.0
167 mM NaCl
Wash Buffer:
100 mM Tris 7.0
500 mM LiCL
1% NP-40
1% Deoxycholic Acid
IP Elution buffer
50 mM NaHCO3
1% SDS To Lysis Buffer and Dilution Buffer, supplement 1 mM PMSF, 0.1 U/ul
Superase-in (Ambion), 1× Proteinase inhibitor (Roche)
To Wash buffer, supplement 1 mM PMSF The above described method has been used on primary human fibroblast cells that ChRIP enriches for known chromatin-associated RNAs such as XIST and KCNQ1ot1 under the same crosslinking condition used in ChIRP experiments, while it does not retrieve abundant cellular RNAs such as mature ribosomal RNAs or GAPDH.

Numerous lncRNAs have been identified that are associated with the chromatin in primary human fibroblast cells or mouse embryonic stem cells, which presumably regulate gene expression or nascent RNA maturation at target genomic sites.

Besides lncRNAs, nascent ribosomal RNAs and mRNAs have been retrieved, as well as sno/sca RNAs involved in their maturation.

The method can provide a list of potentially functionally important of lncRNAs that can be further investigated using techniques such as ChIRP.

Example 7

Resolving RNA: Protein Interactions by ChIRP-Immunoblot (1) Description of ChIRP-Immunoblot The RNA capture strategy used for recovering RNA:chromatin interactions can be extended to recover RNA:protein interactions as well with two modifications to the ChIRP protocol. First, biological samples are cross linked with a reversible crosslinker, such as formaldehyde, such that following recovery of RNA:protein interactions, the crosslinking between the biomolecules may be broken and the protein isolated. Second, proteins are isolated from the recovered material by boiling in SDS-PAGE running buffer and subjected to PAGE. Recovered proteins are resolved by immunoblotting the resulting gel.

(2) Preparing Chromatin Samples for ChIRP-Immunoblot

Immunoblotting of ChIRP-recovered proteins may be performed on proteins that are free of crosslinks. The reason for this is twofold: first, in order to visualize the protein by size on an electrophoretic gel, it must not be covalently linked to other molecules that will shift or impede its electrophoretic mobility; second, the epitope on the protein of interest that is recognized by the primary antibody must be free of chemical modification. Formaldehyde, for example, is a favorable crosslinking agent, as formaldehyde cross links may be reversed by heating to 95° C. for 2×15 min.

(3) ChIRP-Immunoblot Protocol: Protein Isolation

The protocol for ChIRP-immunoblot is identical to that of ChIRP (see above), with the exception of the crosslinking conditions. Protein isolation and immunblotting follows the capture and washing of RNA interactions on streptavidin-functionalized magnetic beads.

First, the remaining wash buffer is removed from the washed magnetic beads.

Next, the beads are resuspended in an appropriate SDS-PAGE buffer, such as Laemmli Buffer supplemented with beta-mercaptoethanol. The volume of the resuspension will depend on the desired final volume of sample that will be run on PAGE. The resuspended beads are placed on a 95° C. heat block for 15 minutes to disrupt the biotin-streptavidin interaction, reverse formaldehyde cross links, and release captured proteins into the buffer.

Following heating, the beads are separated from the suspension on a magnetic strip. The supernatant, which contains the recovered proteins, is collected into a new tube. This protein fraction is subjected to a second 15 min incubation at 95° C. to further reverse cross links. The final sample is stored at 4° C. until it is ready for PAGE.

To recover the remaining protein from the magnetic beads, the beads are resuspended in a second volume of PAGE buffer. The resuspended beads are placed on a 95° C. heat block for an additional 15 minutes, pooled with the first protein fraction, and stored at 4° C. until it is ready for PAGE.

Protein fractions in PAGE buffer are run on PAGE following standard Western blotting procedures.

(4) ChIRP-Immunoblot Application

ChIRP-immunoblot can be used to identify RNA:protein interactions for a given RNA target.

Figure 9:
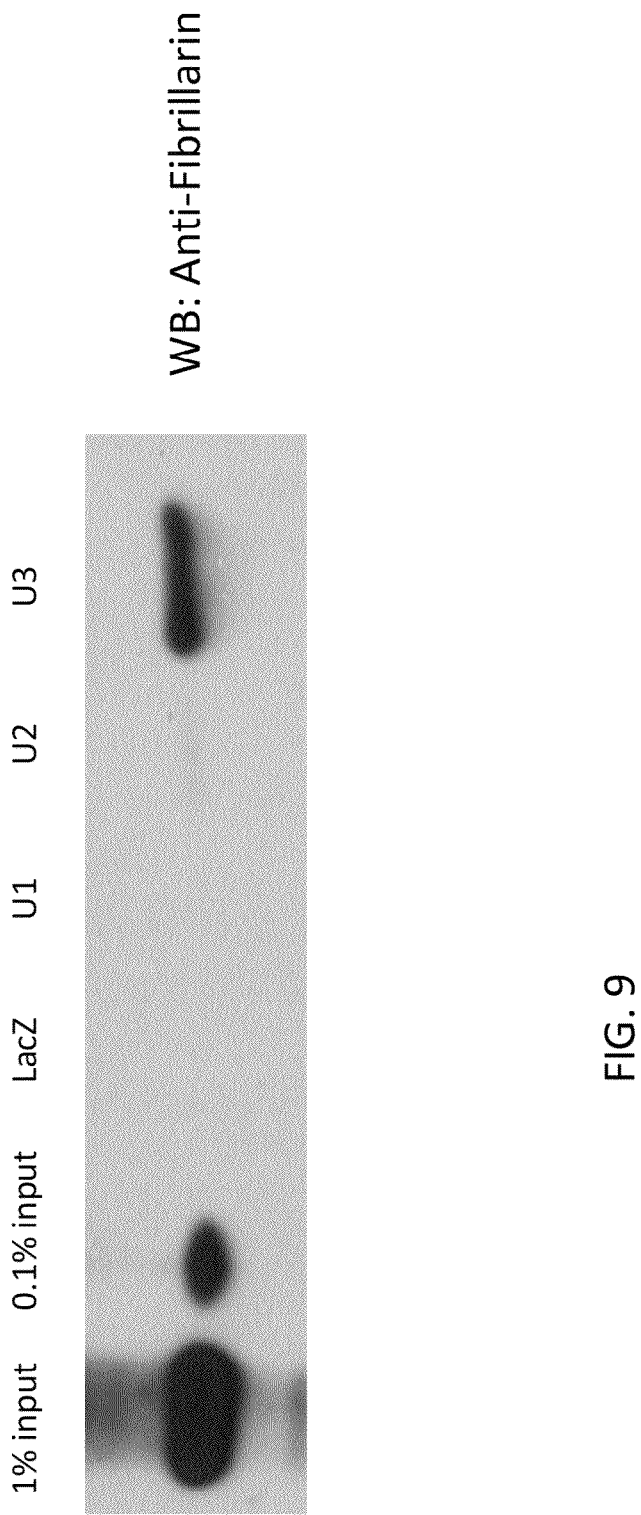
FIG. 9 shows the results of a RIA immunoblot.

Using this method, one we can enrich for small nuclear RNAs U1, U2, and U3 from human cervical cancer cells (HeLa) using biotinylated anti-sense DNA oligos specific against each RNA. As a negative control an oligo against LacZ RNA that is not expressed in human cells is included. Only oligos targeting U3 specifically retrieve the known U3-bound protein fibrillarin, whereas oligos against U1, U2, or LacZ do not retrieve the same protein. See FIG. 9.

Example 9

RIA RNA-Seq

In this case, one may be interested in studying RNA:RNA interactions by isolating all RNAs that are associated with a specific RNA. One can perform the regular ChIRP protocol but instead of isolating both DNA and RNA on can dedicate all eluent for RNA extraction. These RNAs are then subject to quantitave RT-PCR assays, or converted into deep-sequencing libraries using the Ovation-V2 kit (Nugen, C.A., USA) per manufacturer's protocol.

Figure 10:
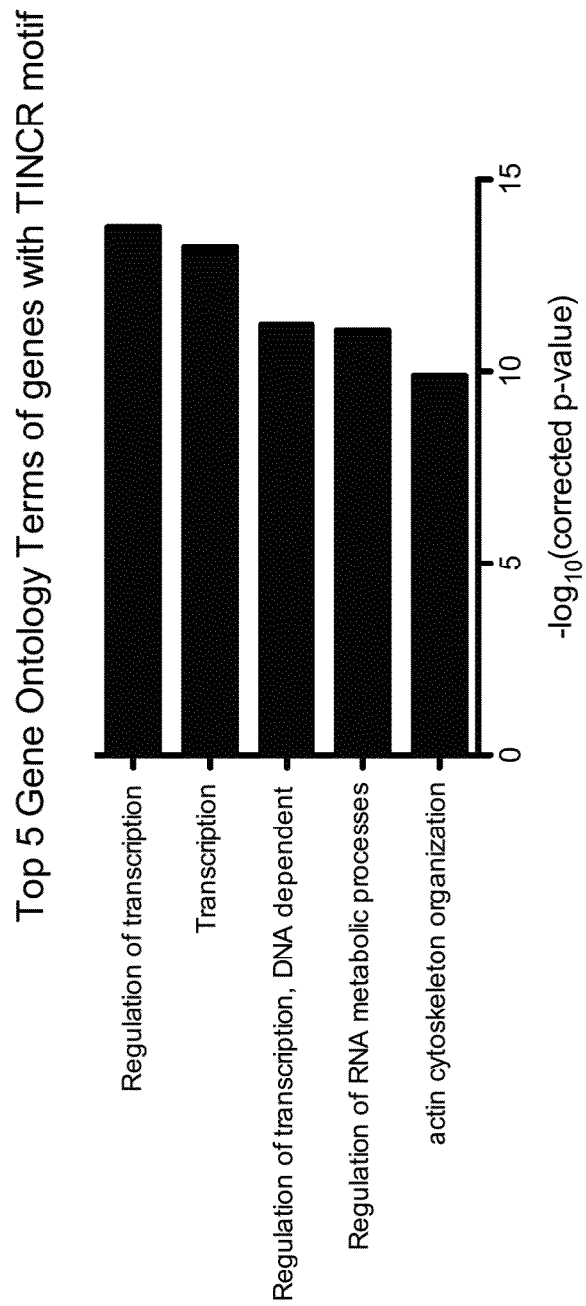
FIG. 10 is a bar graph showing the types of genes that contain the TINCR motif.

This technique was applied to TINCR, a long-noncoding RNA required for keratinocytes differentiation and affect the transcript levels of many skin differentiation genes. Using RIA-seq, it was found that TINCR binds many mRNAs at specific sites. A primary sequence motif could be extracted out of these transcriptome sites and was termed it the "TINCR box." Genes containing the TINCR box strongly enrich in transcription-related GO-terms such as "regulation of transcription" and "RNA metabolism," (see FIG. 10) which is consistent with the hypothesis that TINCR regulate the transcriptional machinery through direct RNA:RNA interaction, thereby affecting the gene expression of many genes involved in the skin differentiation pathway.

Example 10

Domain ChIRP (1) Description of Domain Chirp

Domain ChIRP is a method that allows for RNA domain-specific recovery of RNA-mediated interactions. Domain ChIRP differs from the traditional ChIRP strategy in three specific ways. First, the biotinylated antisense oligos are complementary to specific regions of an RNA target, rather than tiling the entire length of the RNA target. In this way, the complete set of probes is divided into regional probe pools rather than "even" and "odd" probe pools. Second, chromatin samples are sheared by sonication to smaller fragments than that of ChIRP, thus ensuring that the target RNA is fragmented. Lastly, the results of a Domain ChIRP experiment both enumerate RNA-interacting biomolecules (e.g. genomic loci, RNA binding proteins) and also identify the domain of the RNA that is responsible for the enumerated interactions.

(2) Probe Pool Design Strategy for Domain ChIRP

RNA targets are captured by biotinylated antisense probes that tile the RNA of interest. These probes are grouped into probe pools that tile the entire length (internal control pool), RNA regions (regional pool), or specific structural or functional RNA domains (domain-specific pool).

Internal control probe pools: These orthogonal probe pools tile the entire length of the RNA using non-overlapping antisense biotinylated oligos, similar to the "even" and "odd" probe pools of traditional ChIRP. The internal control probe pools serve as a way to control for probe-specific noise and differing probe efficiencies.

Regional probe pools: For an RNA target with unknown structural and/or functional characterization, probes are grouped into regional pools. For example, to capture specific regions of a 600 nt RNA, probes can be grouped into three pools by the 5', middle, and 3' 200 nts.

Domain-specific probe pools: For an RNA target with existing structural and/or functional characterization, probe pools may be rationally designed to recover known structural or functional domains. For example, probe pools may be grouped into known individual exons of the target RNA, around characterized structures such as hairpins, or at a known site of protein interaction.

(3) Preparing Chromatin Samples for Domain ChIRP

After biological samples are crosslinked using a choice crosslinking agent (e.g. formaldehyde, UV, glutaraldehyde), the samples are sonicated to solubilize the biological material and shear nucleic acids. In order for domain ChIRP to recover targeted RNA regions over non-targeted RNA regions, RNA must be fragmented. Depending on the size of the target RNA and the number of domain ChIRP regions, the nucleic acids must be sheared to ~150-500 nt fragments.

The protocol for domain ChIRP is identical to that of traditional ChIRP. Domain ChIRP can be used to map chromatin- and RNA binding protein (RBP)-interaction domains of a target RNA. Furthermore, the strategy of domain ChIRP can also be used to refine ChIRP probe pools. For example, a higher complexity pool of probes leads to more non-target RNA recovery events and therefore more noise in ChIRP data. By whittling probe pools down using domain ChIRP, it is possible to find the best probes to use for targeting an RNA and recovering its bimolecular interaction partners.

The invention claimed is:

1. A method of sample analysis comprising:
   a) cross-linking the contents of a cell using a crosslinking agent to produce cross-linked ribonucleotide complexes;
   b) fragmenting said cross-linked ribonucleotide complexes to produce complexes comprising protein, RNA fragments and genomic DNA fragments;
   c) contacting said complexes with a plurality of non-overlapping oligonucleotides that comprise an affinity tag and that are complementary to a specific target RNA of said cell under high stringency conditions;
   d) isolating complexes that contain said oligonucleotides using the affinity tag of said oligonucleotides to produce isolated complexes;
   e) treating the isolated complexes with RNAse and a protease, thereby enzymatically releasing said genomic DNA fragments from said isolated complexes to produce released genomic DNA;
   f) sequencing said released genomic DNA to identify an occupancy site for an RNA.

2. The method of claim 1, wherein said crosslinking agent is glutaraldehyde or formaldehyde.

3. The method of claim 1, wherein said fragmenting is done enzymatically, chemically or physically.

4. The method of claim 1, wherein said fragmenting is done by sonicating.

5. The method of claim 1, wherein said fragmenting produces fragments having an average size in the range of 100 bp to 500 bp in length.

6. The method of claim 1, wherein said oligonucleotides hybridize to sites in said specific RNA that are spaced along said RNA by at least 2 nucleotides.

7. The method of claim 1, wherein said oligonucleotides are in the range of 15 to 30 nucleotides in length and temperature matched.

8. The method of claim 1, wherein said oligonucleotides hybridize to mRNA.

9. The method of claim 1, wherein said oligonucleotides hybridize to non-coding RNA.

10. The method of claim 1, wherein said oligonucleotides hybridize to lncRNA.

11. The method of claim 1, wherein said high stringency conditions include an incubation at least 37° C. for at least 4 hours.

12. The method of claim 1, wherein said oligonucleotides are biotinylated.

13. The method of claim 1, wherein said isolating is done using a support that comprises a ligand for said affinity tag.

14. The method of claim 13, wherein said support is streptavidin.

* * * * *